(12) United States Patent
Loeffler et al.

(10) Patent No.: US 9,120,731 B2
(45) Date of Patent: Sep. 1, 2015

(54) PROCESS FOR PREPARING POLYETHER ALCOHOLS

(75) Inventors: Achim Loeffler, Speyer (DE); Michael Stoesser, Neuhofen (DE); Wolfgang Loth, Bad Duerkheim (DE); Ralf Boehling, Lorsch (DE); Sirus Zarbakhsh, Hong Kong (CN)

(73) Assignee: BASF SE, Ludwigshafen (DE)

( * ) Notice: Subject to any disclaimer, the term of this patent is extended or adjusted under 35 U.S.C. 154(b) by 282 days.

(21) Appl. No.: 13/813,300

(22) PCT Filed: Aug. 8, 2011

(86) PCT No.: PCT/EP2011/063646
§ 371 (c)(1),
(2), (4) Date: Jan. 30, 2013

(87) PCT Pub. No.: WO2012/020005
PCT Pub. Date: Feb. 16, 2012

(65) Prior Publication Data
US 2013/0131389 A1 May 23, 2013

(30) Foreign Application Priority Data
Aug. 9, 2010 (DE) .................. 10 2010 039 090

(51) Int. Cl.
*C07C 41/02* (2006.01)
*C08G 65/26* (2006.01)
(52) U.S. Cl.
CPC ............ *C07C 41/02* (2013.01); *C08G 65/2696* (2013.01)
(58) Field of Classification Search
CPC .................. C07C 41/02; C08G 65/2696
See application file for complete search history.

(56) References Cited

U.S. PATENT DOCUMENTS

| 5,470,813 A | 11/1995 | Le-Khac |
| 2002/0032121 A1 | 3/2002 | Grosch et al. |

(Continued)

FOREIGN PATENT DOCUMENTS

| EP | 0 700 949 | 3/1996 |
| EP | 0 743 093 | 11/1996 |

(Continued)

OTHER PUBLICATIONS

Edens, M., et al., "Applicantions of Block Copolymer Surfactants," Developments in Block Copolymer Science and Technology, pp. 326-340, (Jan. 1, 2004).

(Continued)

*Primary Examiner* — Rosalynd Keys
(74) *Attorney, Agent, or Firm* — Oblon, McClelland, Maier & Neustadt, L.L.P.

(57) ABSTRACT

What is proposed is a process for preparing polyether alcohols by conversion of the following reactants: a) one or more alkylene oxides and optionally carbon dioxide and b) one or more H-functional starter substances, in the presence of a catalyst, to form a liquid reaction mixture, in a reaction unit (1), which is characterized in that the reaction unit (1) has internals (2) which form a multitude of microstructured flow channels which bring about multiple splitting of the liquid reaction mixture into component flow paths and recombination thereof in altered arrangement, the multiple splitting and recombination being repeated several times and the microstructured flow channels having a characteristic dimension which is defined as the greatest possible distance of any particle in the liquid reaction mixture from the wall of a flow channel closest to the particle, in the range from 20 to 10 000 μm, the result being that the flow profile of the liquid reaction mixture approximates to ideal plug flow as a result of the microstructured flow channels.

18 Claims, 2 Drawing Sheets

(56) References Cited

U.S. PATENT DOCUMENTS

Figure 1:
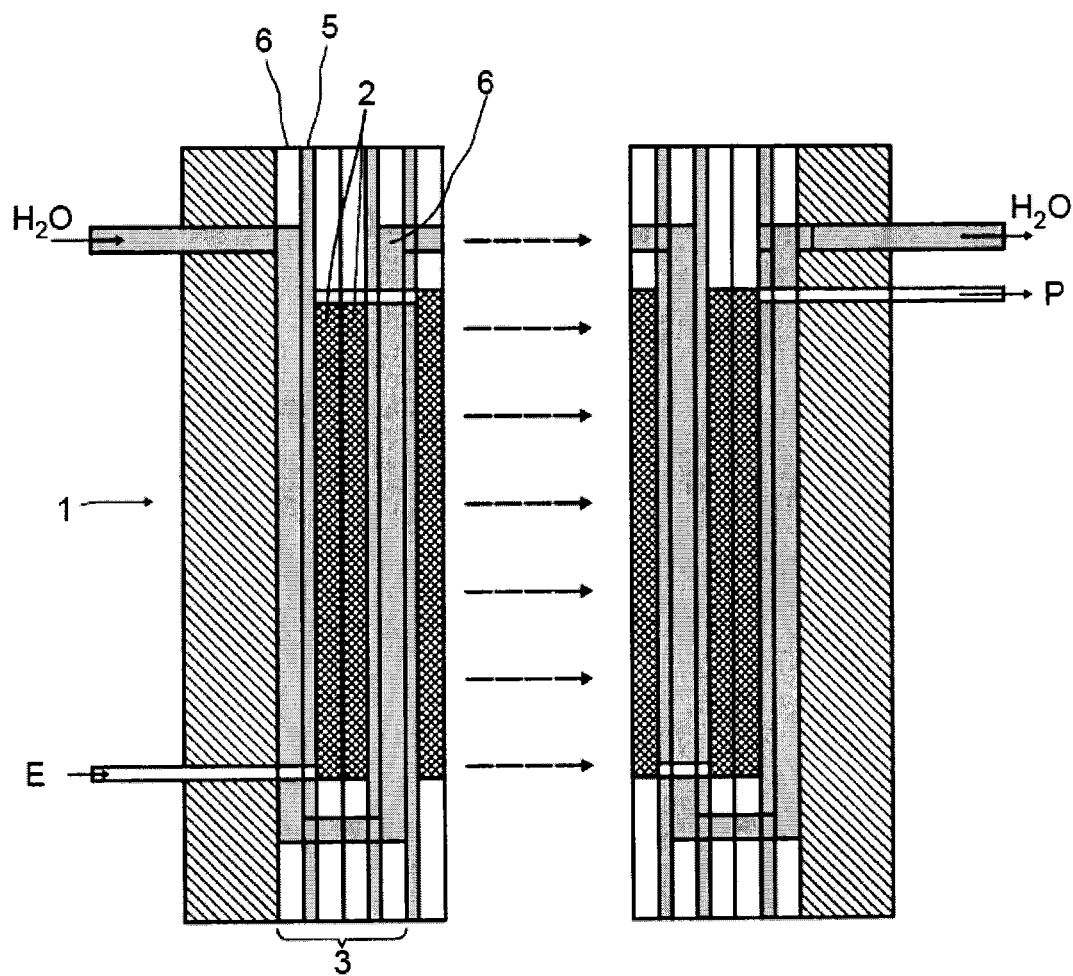

| | | |
|---|---|---|
| 2003/0199670 A1 | 10/2003 | Grosch et al. |
| 2004/0156762 A1 | 8/2004 | Schuppich et al. |
| 2005/0245628 A1 | 11/2005 | Hubel et al. |
| 2009/0203874 A1 | 8/2009 | Loeffler et al. |
| 2011/0213177 A1 | 9/2011 | Mattke et al. |
| 2011/0218259 A1 | 9/2011 | Eling et al. |
| 2011/0218262 A1 | 9/2011 | Eling et al. |
| 2011/0218324 A1 | 9/2011 | Zarbakhsh et al. |
| 2011/0224396 A1 | 9/2011 | Ahmadnian et al. |
| 2011/0224397 A1 | 9/2011 | Ostrowski et al. |
| 2011/0263737 A1 | 10/2011 | Fricke et al. |
| 2011/0263742 A1 | 10/2011 | Zarbakhsh et al. |
| 2011/0269863 A1 | 11/2011 | Kunst et al. |
| 2011/0282027 A1 | 11/2011 | Deglmann et al. |
| 2012/0130134 A1 | 5/2012 | Schopohl et al. |
| 2012/0197042 A1 | 8/2012 | Schoenfelder et al. |
| 2013/0023700 A1 | 1/2013 | Chilekar et al. |

FOREIGN PATENT DOCUMENTS

| | | |
|---|---|---|
| EP | 0 761 708 | 3/1997 |
| EP | 1 586 372 | 10/2005 |
| JP | 4 145123 | 5/1992 |
| WO | 97 40086 | 10/1997 |
| WO | 00 74845 | 12/2000 |
| WO | 02 09866 | 2/2002 |
| WO | 2007 135154 | 11/2007 |
| WO | 2011 085772 | 7/2011 |
| WO | 2011 160296 | 12/2011 |
| WO | 2011 160797 | 12/2011 |

OTHER PUBLICATIONS

Amador, C., et al., "Flow distribution in different microreactor scale-out geometries and the effect of manufacturing tolerances and channel blockage," Chemical Engineering Journal, vol. 101, pp. 379-390, (2004).

International Search Report Issued Oct. 17, 2011 in PCT/EP11/63646 Filed Aug. 8, 2011.

PROCESS FOR PREPARING POLYETHER ALCOHOLS

The invention relates to a process for preparing polyether alcohols.

Polyether alcohols may be polyether polyols, which are used in particular as raw materials for the production of polyurethanes, or else may be polyether monools, which are employed in various fields of application, especially as surface-active substances, laundry detergents and cleaners, in mining, in construction, as oilfield chemicals, in textiles or leather processing, as coatings, as formulation auxiliaries for crop protection agents, as cosmetics and personal care products, as formulation auxiliaries for human and animal nutrition, for pigments, for drugs or as fuel additives.

The preparation of polyether alcohols in a reaction unit having a plurality of layers arranged parallel to one another and being microstructured is known.

EP-A 1 586 372 describes a microstructured reactor and its use in a process for preparing polyether alcohols by a ring-opening addition reaction of alkylene oxides in the presence of a solid catalyst, with the chemical process taking place in spaces which are formed by two or more essentially plane-parallel plates or layers and mixing of the starting materials occurring individually in a single liquid phase in each reaction channel, a heat exchange apparatus being provided and the reactor being operated at pressures of up to 800 bar and temperatures in the range from 30 to 400° C. In this way, the potential of very high reaction rates resulting from high alkylene oxide pressures can be optimally utilized and polyether alcohols of uniform quality and having a low content of by-products can be prepared.

However, microstructured apparatuses are very difficult structures; even in manufacture, the tolerances are such that, especially for reaction systems having an appreciably increasing viscosity over the reaction time, as is the case in the present preparation of polyether polyols, the pressure drop in the individual capillaries relative to one another leads to maldistribution of the mass flows. This problem is comprehensively described by C. Amador et al. in Chem. Eng. J. 101 (2004)1-3, pages 379-390. The avoidance of maldistributions in tube apparatuses connected in parallel was studied as early as the 1980s. Approaches which promote equal distribution even in the case of viscosity-increasing systems have been developed. In the same way as the pressure drops in the individual capillaries have to be taken into account in the feeding of starting materials into the microstructured reactor, this effect also has to be taken into account in the introduction of further material.

In addition, the process for preparing polyether polyols requires very high pressures, which force a reactor design capable of withstanding up to several hundred bar.

EP-A 06 114 369 discloses an improved process for preparing polyether polyols in a reaction unit having a plurality of layers arranged parallel to one another and being microstructured, said process ensuring improved equal distribution of the reaction mixture to the individual reaction channels, through the provision of a distribution device before the introduction of the starting materials and the catalyst to the channels, and, at the end thereof, of a collection device for the reaction mixture.

EP-A 06 114 369 describes a process for preparing polyether polyols by reaction of the following starting materials:

a) one or more alkylene oxides and optionally carbon dioxide and also b) one or more H-functional starter substances, in the presence of a catalyst in a reaction unit having a plurality of layers A, B which are arranged in parallel above one another and are microstructured so that each layer has a multiplicity of channels which are arranged parallel to one another and form a continuous flow path from one side of the plate to the opposite side of this, in which part of the starting materials or all starting materials and optionally the catalyst are premixed at a temperature below the temperature of the reaction in a mixer outside the channels and the mixture is subsequently fed into the channels in the layers A on one side of this and the reaction mixture is taken off on the other side of this and a heat transfer medium is fed into the channels of planes B arranged alternately to the planes A on one side of these and is taken off again on the other side of these, wherein a distribution device for introduction of the starting materials and the catalyst is provided at one end of the channels of the planes A and a collection device for the reaction mixture is provided at the other end of these.

In the light of this, it was an object of the invention to ensure a further improvement in the equal distribution of the mass flows in a process for preparing polyether alcohols, and thereby to achieve further improvements in yields and selectivities and also in product properties.

This object is achieved by means of a process for preparing polyether alcohols by reaction of the following starting materials:

a) one or more alkylene oxides and optionally carbon dioxide and also b) one or more H-functional starter substances, in the presence of a catalyst, to form a liquid reaction mixture, in a reaction unit, wherein the reaction unit has internals which form a multiplicity of microstructured flow channels, which effect multiple splitting of the liquid reaction mixture into component flow pathways and renewed recombining thereof in altered arrangement, the multiple splitting and renewed recombining being repeated a multiplicity of times, and the microstructured flow channels having a characteristic dimension, defined as the greatest possible distance of any particle in the liquid reaction mixture to the flow channel wall closest to the particle, in the range from 20 to 10 000 µm, so that the flow profile of the liquid reaction mixture through the microstructured flow channels is approximate to an ideal plug flow.

It has been found that an improvement in the equal distribution of the reaction mixture over the entire reaction front is possible through the use in the reaction unit of internals which form microstructured flow channels which function as static mixers and which have a characteristic dimension as defined above.

The devices in question are what are called split-and-recombine mixers, in other words mixers characterized by stages of recurring separation and combination of streams.

The term flow channel or else flow pathway as used in the present context can be defined such that a flow channel or flow pathway encompasses all particles of the liquid reaction mixture that are not separated from one another by internals or walls radially to the flow direction. A flow channel or flow pathway connects mixing sites to one another, and distributors to mixing sites.

Mixers which form microstructured flow channels are also known as micromixers.

Essential for the present invention is the use of internals which form microstructured flow channels having a characteristic dimension in the range from 20 to 10 000 μm and thereby approximate the flow profile of the liquid reaction mixture away from a parabolic flow profile to an ideal plug flow.

The preparation of the polyalcohols in the process of the invention is carried out by reaction of the following starting materials:
a) one or more alkylene oxides and optionally carbon dioxide and also
b) one or more H-functional starter substances,
in the presence of a catalyst.

As starting materials a), it is possible to use all known alkylene oxides. Preference is given to using one or more substances selected from the following listing: ethylene oxide, propylene oxide, butylene oxide, pentene oxide, glycidyl ether, hexene oxide and/or styrene oxide, preferably ethylene oxide, propylene oxide, carbon dioxide, and mixtures thereof. In the case of butylene oxide, pentene oxide and hexene oxide, all isomers can be used in pure form or as mixtures of the isomers.

Carbon dioxide can preferably be used in an amount of up to 25% by weight, based on the weight of the polyether alcohol.

As H-functional starter substance or substances, preference is given to using one or more alcohols having a functionality of from 1 to 8, preferably from 2 to 8, particularly preferably from 2 to 6, more preferably from 2 to 4.

One or more substances from the following listing can be used for this purpose: ethylene glycol, propylene glycol, diethylene glycol, dipropylene glycol, glycerol, trimethylolpropane, pentaerythritol, sucrose, saccharose, glucose, fructose, mannose, sorbitol, hydroxyalkylated (meth)acrylic acid derivatives and alkoxylated derivatives of the abovementioned H-functional starter substances up to a molecular weight of about 1500 D. Furthermore, primary and/or secondary amines and also thiols can serve as starters. It is also possible to use compounds which comprise both OH and also allyl or vinyl groups, for example allyl alcohol and its etherification products with polyhydric alcohols, and which can serve as starting materials in a subsequent free-radical polymerization.

As H-functional starter substances, it is preferred to use one or more alcohols having a functionality of from 1 to 8.

As H-functional starter substance or substances, it is also possible to use one or more alcohols having a functionality of 1 and having the general formula R—OH, where R is a saturated or unsaturated alkyl, aryl, aralkyl or alkylaryl radical having from 1 to 60, preferably from 1 to 24, carbon atoms, in particular one or more substances from the following listing: methanol, butanol, hexanol, heptanol, octanol, decanol, undecanol, dodecanol or tridecanol, tetradecanol, pentadecanol, hexadecanol, heptadecanol, octadecanol, butenol, hexenol, heptenol, octenol, nonenol, decenol, undecenol, vinyl alcohol, allyl alcohol, geraniol, linalool, citronellol, phenol or nonylphenol. As alkylaryl radicals, particular preference is given to those having $C_4$-$C_{15}$-alkyl groups.

As H-functional starter substances it is preferred to use one or more alcohols having a functionality of from 2 to 8, with particular preference from 2 to 4, with further preference from 2 to 3, and especially one or more substances from the following listing: ethylene glycol, propylene glycol, glycerol, trimethylolpropane and pentaerythritol.

As catalysts, it is possible to use, in particular, multimetal cyanide complex catalysts or alkali metal and alkaline earth metal hydroxides, preferably potassium hydroxide and cesium hydroxide, and also other basic catalysts such as alkali metal alkoxides or amines. Apart from soluble basic catalysts, it is also possible to use insoluble basic catalysts such as magnesium hydroxide or hydrotalcite. Furthermore, Brönsted-acid catalysts, e.g. montmorillonite, or Lewis-acid catalysts, e.g. boron trifluoride, are also suitable.

Suitable multimetal cyanide complex catalysts are, in particular, double metal cyanide catalysts (DMCs) which are known and are described, for example, in WO 01/083107. They usually have the general formula (I)

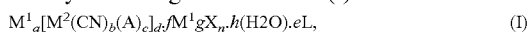
$$M^1{}_a[M^2(CN)_b(A)_c]_d\cdot fM^1gX_n\cdot h(H2O)\cdot eL, \qquad (I)$$

where
$M^1$ is a metal ion selected from the group consisting of $Zn^{2+}$, $Fe^{2+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$,
$M^2$ is a metal ion selected from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, $Ir^{3+}$,
and $M^1$ and $M^2$ are identical or different,
A is an anion selected from the group consisting of halide, hydroxide, sulfate, carbonate, cyanide, thiocyanate, isocyanate, cyanate, carboxylate, oxalate and nitrate,
X is an anion selected from the group consisting of halide, hydroxide, sulfate, carbonate, cyanide, thiocyanate, isocyanate, cyanate, carboxylate, oxalate and nitrate,
L is a water-miscible ligand selected from the group consisting of alcohols, aldehydes, ketones, ethers, polyethers, esters, ureas, amides, nitriles, lactones, lactams and sulfides, and
a, b, c, d, g and n are selected so that the compound is electrically neutral and
is the coordination number of the ligand or 0,
f is a fraction or integer greater than or equal to 0 and
h is a fraction or integer greater than or equal to 0.

The preparation of these compounds is carried out by generally known methods, by combining the aqueous solution of a water-soluble metal salt with the aqueous solution of a hexacyanometalate compound, in particular a salt or an acid, hereinafter also referred to as starting material solutions, and, if appropriate, adding a water-soluble ligand thereto during or after combination of the solutions. Such catalysts and their preparation are described, for example, in EP 862,947 and DE 197,42,978. Amorphous DMC catalysts with high activity are described in the following patents and can likewise be employed:

JP-A 4 145 123, US-A 5 470 813, EP-A 700,949, EP-A 743 093, EP-A 761 708 and WO 97/40086 disclose DMC catalysts which, through the use of tert-butanol as an organic complex ligand (alone or in combination with a polyether (EP-A 700 949, EP-A 761 708, WO 97/40086)), reduce further the proportion of monofunctional polyethers with terminal double bonds in the preparation of polyether polyols.

The complicated removal of multimetal cyanide compounds from the polyether alcohol after the preparation can thus be dispensed with. However, it is also possible to use a larger amount of multimetal cyanide compounds and to reduce the amount of the multimetal cyanide compound in the polyol after the synthesis of the polyether alcohol to such an extent that the polyether alcohol comprises the amount of multimetal cyanide compounds desired for further processing.

The multimetal cyanide compounds are preferably used in the form of suspensions in which the multimetal cyanide compounds are suspended in organic compounds, preferably alcohols. In the process of the invention, one possibility is to disperse the catalyst either in an intermediate or in the end product of the synthesis. The catalyst suspension should have a concentration in the range from 0.5 to 10%.

The DMC catalysts are highly active. DMC catalysts have hitherto been used first and foremost in semibatch reactors or continuous backmixed reactors (generally stirred tank reactors). However, this reactor concept does not take account of the possible high reaction rate of the DMC catalysts; rather, the maximum reaction rate is frequently limited by the limited heat removal rate of these types of reactor, with both reactors having internal cooling coils and those having external heat exchangers being limited. The consequence is that the reaction can no longer be carried out at a constant temperature at high alkylene oxide introduction rates, which can be particularly critical in the preparation of polyetherols for polyurethane applications since, firstly, undesirable odorous substances can occur as a result of thermal decomposition reactions and, secondly, a deterioration in the foam properties can occur as a result of relatively high-molecular-mass by-products that are formed.

The concentration of the catalysts is, if they are multimetal cyanide complex catalysts, frequently in the range from 5 to 5000 ppm, based on the total weight of the starting materials, depending on the H-functional starter substances used.

Alkali metal hydroxides or alkoxides as catalysts are usually used in higher concentrations of, for example, from 100 to 50 000 ppm, based on the total weight of the starting materials.

Where these basic catalysts are used, the reaction part itself is followed by a processing operation in which the polyols are neutralized and the metal salt or metal hydroxides are removed from the polyol. Neutralization takes place generally with aqueous organic or inorganic acids such as, for example, $CO_2$, sulfuric acid, phosphoric acid, hydrochloric acid, lactic acid, acetic acid or similar compounds. The salts formed are then either precipitated and isolated by filtration or centrifugation, or isolated in aqueous phase by ion exchangers or coalescers. Isolation is generally followed by drying, in which, at temperatures between 80 and 160° C. and at a reduced pressure of 5-500 mbar and, as and when required, with addition of an entraining gas such as steam or nitrogen, the residual water is removed and the polyol is freed from disruptive secondary components such as odorous substances, etc. This last processing step, the removal of odorous substances under reduced pressure and with the aid of an entraining gas, is generally also applied in respect of catalysts which do not have to be removed from the reaction mixture, such as, for example, DMC catalysts or amines, e.g. imidazoles, dimethylalkanolamines or other catalysts.

In many cases it is advantageous, together with or instead of the stated alcohols as H-functional starter substances, to use the reaction products thereof with alkylene oxides, especially with propylene oxide, preferably reaction products having a molar mass of up to 500 g/mol. In this case, the addition reaction of the alkylene oxides for preparing the reaction products may take place with any desired catalysts, as for example with basic or Lewis-acid catalysts.

It is possible either to use only a single alkylene oxide as starting material a) or to use a plurality of alkylene oxides, in which case either a blockwise addition in which the alkylene oxides are added on individually in succession or a random addition in which the alkylene oxides are introduced together is possible. Mixed forms in which both blockwise and random sections are incorporated into the polyether chain are also possible.

It is possible for the reaction of the one or more alkylene oxides to take place with addition of a comonomer or carbon dioxide, where the comonomer is a cyclic anhydride, a lactone, or any mixture thereof.

The starting materials are preferably used in a ratio of 1-300 equivalents of starting materials a) (one or more alkylene oxides and optionally carbon dioxide), per H-functional group from the starting materials b).

In the process of the invention, preferably part of the starting materials or preferably all starting materials and optionally the catalyst are firstly premixed outside the channels, with it being ensured that the temperature during premixing is lower than the temperature of the subsequent reaction.

As mixer which is located outside the reactor and in which part of the starting materials or all starting materials and optionally the catalyst are premixed, preference is given to using a microstructured mixer.

Mixers suitable for this purpose are, for example, laminar diffusion mixers, multilamination mixers, micromixers having structured walls or split-recombine mixers.

In laminar diffusion mixers, the mixing of substreams of the fluid which has been divided into a multiplicity of microscopically small flow lamellae having a thickness in the range from 10 to 2000 µm or from 20 to 1000 µm or from 40 to 500 µm on a microstructure occurs exclusively by molecular diffusion perpendicular to the principal direction of flow. An approximate design of the mixer can be effected via the Fourier number $Fo=\tau/\tau_D$. If the residence time $\tau$ is at least in the order of magnitude of the diffusion time $\tau_D$ for transverse mixing, i.e. if the Fourier number is at least 1, virtually complete molecular mixing is achieved at the outlet of the mixer.

Laminar diffusion mixers can be configured as simple T- or Y-mixers or as multilamination mixers. In the case of a T- or Y-mixer, the two substreams to be mixed are fed via a T- or Y-shaped arrangement into a single channel. A critical parameter for determining the transverse diffusion path $S_{diff}$ is the channel width $\delta_C$. For typical channel widths in the range from 100 µm to 1 mm, very short mixing times of less than 100 ms are obtained for gases, while the mixing times are in the range of minutes for liquids. In the case of mixing of liquids, as in the present process, it is advantageous to additionally support the mixing process, for example by means of flow-induced transverse mixing.

In multilamination mixers, the substreams to be mixed are geometrically divided in a divider into a multiplicity of flow threads and are then fed alternately into lamellae of the mixing section at the outlet of the divider. In the case of liquids, mixing times in the range of seconds are achieved in classical multilamination mixers. Since this is not sufficient for some applications (e.g. in the case of fast reactions), the basic principle has been developed further so that the flow lamellae are once again additionally focused geometrically or hydrodynamically. Geometric focusing is achieved by means of a constriction in the mixing section and hydrodynamic focusing is achieved by means of two lateral streams which flow perpendicularly into the main stream and thus further compress the flow lamellae. The focusing described allows lateral dimensions of the flow lamellae of a few microns to be achieved, so that even liquids can be mixed within a few 10s of microseconds.

In micromixers having structured walls, secondary structures, for example flutes or bridges, are arranged on the channel walls at a particular angle to the principal direction of flow, preferably 45° or 90°.

Split-recombine mixers have stages of recurring separation and combination of streams. In each of these stages, the number of lamellae is successively doubled and the thickness of the lamellae and the diffusion path are thereby halved.

It can be advantageous firstly to premix an alkylene oxide, for example propylene oxide, and the catalyst, for example, a multimetal cyanide complex catalyst, and only to add the H-functional starter substance or substances in a second mixing step.

The residence time in the premixing step is preferably in the range from 1 to 300 seconds.

The process is advantageously carried out continuously.

The invention also provides a process for preparing polyether alcohols by reaction of the following starting materials:
a) one or more alkylene oxides and optionally carbon dioxide and also
b) one or more H-functional starter substances
in the presence of a catalyst,
in block operation with
two or more reaction units corresponding to the above definition being provided, wherein
1) the starting materials a) and b) are fed to a first reaction unit to give a first reaction mixture,
2) the first reaction mixture is preferably cooled/heated after leaving the first reaction unit,
3) one or more further starting materials different from the starting materials introduced in process step 1) or the same starting materials as in process step 1) in a mixing ratio different from that in process step 1) are mixed in to give a second reaction mixture and the second reaction mixture
4) is fed to a second reaction unit,
and the reaction mixture obtained therefrom is optionally fed to a further reaction unit, with the process steps 2) and 3) being repeated accordingly.

In one process variant, a multimetal cyanide complex catalyst is used as catalyst. In this case, the reaction discharge from the single reaction unit or the last of the plurality of reaction units is fed to a membrane separation unit and separated into a catalyst-rich stream (retentate) and a catalyst-free stream (permeate or filtrate). An increase in the concentration of the catalyst by, in particular, a factor of from 2 to 100 is possible by means of the membrane process. The catalyst concentrate is recycled to the reactor, with small amounts, in particular in the range from 0.1 to 3%, being discharged in order to avoid accumulation of residues. The filtrate (product) is taken from the reaction system.

Suitable membrane processes are microfiltration or cross-flow filtration and ultrafiltration. The membranes used have pore diameters in the range from 1 nm to 1 µm, preferably from 2 nm to 0.1 µm. The separation layers of the filter membranes can comprise, for example, organic polymers, ceramic, metal, carbon or combinations thereof and have to be stable in the reaction medium at the process temperature. Preference is given to inorganic membranes. For mechanical reasons, the separation layers are generally applied to a single-layer or multilayer porous substructure which consists of the same material as the separation layer or at least one different material. Examples are:

| Separation layer | Substructure (coarser than separation layer) |
|---|---|
| Metal | Metal |
| Ceramic | Metal, ceramic or carbon |
| Polymer | Polymer, metal, ceramic or ceramic on metal |
| Carbon | Carbon, metal or ceramic |

As ceramic, it is possible to use, for example, $\alpha$-$Al_2O_3$, $ZrO_2$, $TiO_2$, SiC or mixed ceramic materials, and polymers which can be used are, for example, polytetrafluoroethylene, polyvinylidene fluoride, polysulfones, polyether sulfones, polyether ether ketones or polyamides.

The invention also provides for the use of the polyether alcohols prepared by the process described above for producing polyurethanes.

Furthermore, the invention also provides for the use of the polyether alcohols prepared by the process described above as: surface-active substances, laundry detergents and cleaners, mining chemicals, oilfield chemicals, textile additive, leather processing auxiliaries, coating additives, formulation auxiliaries for crop protection agents, auxiliaries for cosmetics and personal care, formulation auxiliaries for human and animal nutrition, formulation auxiliaries for pigments, formulation auxiliaries for drugs or fuel additives.

Compared to known processes, the process of the invention achieves, in particular, further avoidance or reduction of maldistributions in the channels of a microstructured reactor. Accordingly, improvements in yields and selectivities and in product properties can be achieved by means of the process of the invention. Particularly when using DMC catalysts and low molecular weight, polyfunctional starters, the process of the invention enables complete conversion to be achieved and the content of high molecular weight by-products to be reduced compared to known processes which lead to no conversion or a very low conversion. Compared to products from known processes, the products obtained by the process of the invention have, in particular, a lower viscosity at the same molar mass.

In one preferred embodiment of the invention, at least one reactor is used which has the residence time characteristics of a plug flow.

In the presence of plug flow in a tube reactor—or in the present instance a flow channel—it is possible for the condition of the reaction mixture (for example temperature, composition, etc.) to vary in the direction of flow, whereas for each individual cross section perpendicular to the flow direction, the condition of the reaction mixture is the same. Accordingly, all of the volume elements entering the tube have the same residence time in the reactor. From a pictorial viewpoint, the liquid flows through the tube as if it were a series of plugs gliding gently through the tube. In addition, as a result of the intensified mass transport perpendicularly to the flow direction, cross-mixing is able to compensate the thermal and concentration gradients perpendicular to the direction of flow.

In spite of the mostly laminar flow, therefore, backmixing can be avoided and it is possible to achieve a narrow residence time distribution, similarly to the case with an ideal flow tube.

Furthermore, the internals used according to the invention that form microstructured flow channels ensure a high degree of thermal homogeneity perpendicular to the flow direction. In principle, each differential volume element has substantially the same temperature over the particular flow cross section. The maximum allowable temperature differences in a flow cross section are dependent on the desired product properties: the maximum temperature difference in one flow cross section is preferably less than 40° C., more preferably less than 20° C., with further preference less than 10° C., and very preferably less than 5° C.

Materials which have been found to be advantageous for the internals and reaction units to be used in accordance with the invention include stainless steels which are austenitic in the low-temperature range, such as 1.4541 and 1.4571, commonly known as V4A and as V2A, respectively, and also stainless steels of the US types SS316 and SS317Ti. At higher temperatures and under corrosive conditions, PEEK (polyether ether ketones: thermoplastics of high temperature stability) is likewise suitable. It is also possible, though, to use more corrosion-resistant Hastelloy® grades, glass or ceramic as materials and/or corresponding coatings, such as, for example, $TiN_3$, Ni-TTFE, Ni-PFA or the like.

It is preferred to use internals whose effect is that the multiple splitting of the liquid reaction mixture into component flow pathways and renewed recombining is repeated 10 to 10 000 times.

It is preferred to use internals which have a characteristic dimension of the microstructured flow channels in a range from 40 to 6000 µm, preferably in a range from 50 to 4000 µm.

The invention is not restricted in terms of the specific technical embodiment of the internals used that form microstructured flow channels. It is possible to use all known static mixers which fulfill the features defined above, i.e., which have in particular a characteristic dimension, defined as the greatest possible distance of any particle in the liquid reaction mixture to the flow channel wall closest to the particle, in the range from 20 to 10 000 μm.

These internals may preferably be internals which are reaction plates, with two or more reaction plates arranged in parallel above one another and in the principal direction of flow through the reactor unit to each form one reactor module, and the reaction unit has one or more reactor modules, and each reaction plate has a multiplicity of slots of constant or variable width which are arranged parallel to one another and at a nonzero angle α to the principal direction of flow, and the immediately adjacent reaction plate has a multiplicity of geometrically corresponding slots which are arranged at the same angle α but with its sign reversed, with the slots of all reaction plates arranged one above another forming a flow channel, with feeding of the starting materials into the flow channel and removal of the product mixture from the flow channel, with one separator sheet arranged parallel to each of the reaction plates, on both sides of the reactor module, each separator sheet completely closing off the slots, and with one or more cooling or heating plates adjacent to each separator sheet, on the side of the separator sheet opposite to the reactor module, with a heat transfer medium circulating through the one or more cooling or heating plates.

Reactors with internals of this kind are available, for example, from BTS-Ehrmann under the name Miprowa® reactors.

The angle α is preferably 45°.

With further preference, internals as described above are used which have two or more cooling or heating plates, with each cooling or heating plate having a multiplicity of slots of constant or variable width that are arranged parallel to one another and at a nonzero angle α to the principal direction of flow of the heat transfer medium, and the immediately adjacent cooling or heating plate having a multiplicity of geometrically identical slots which are arranged at the same angle α but with its sign reversed, and where the slots of all the cooling or heating plates arranged one above another form a flow channel, with the heat transfer medium being fed into the flow channel and the heat transfer medium being removed at the other end of the flow channel.

The invention is elucidated in more detail below with reference to a drawing and to examples.

Figure 2:
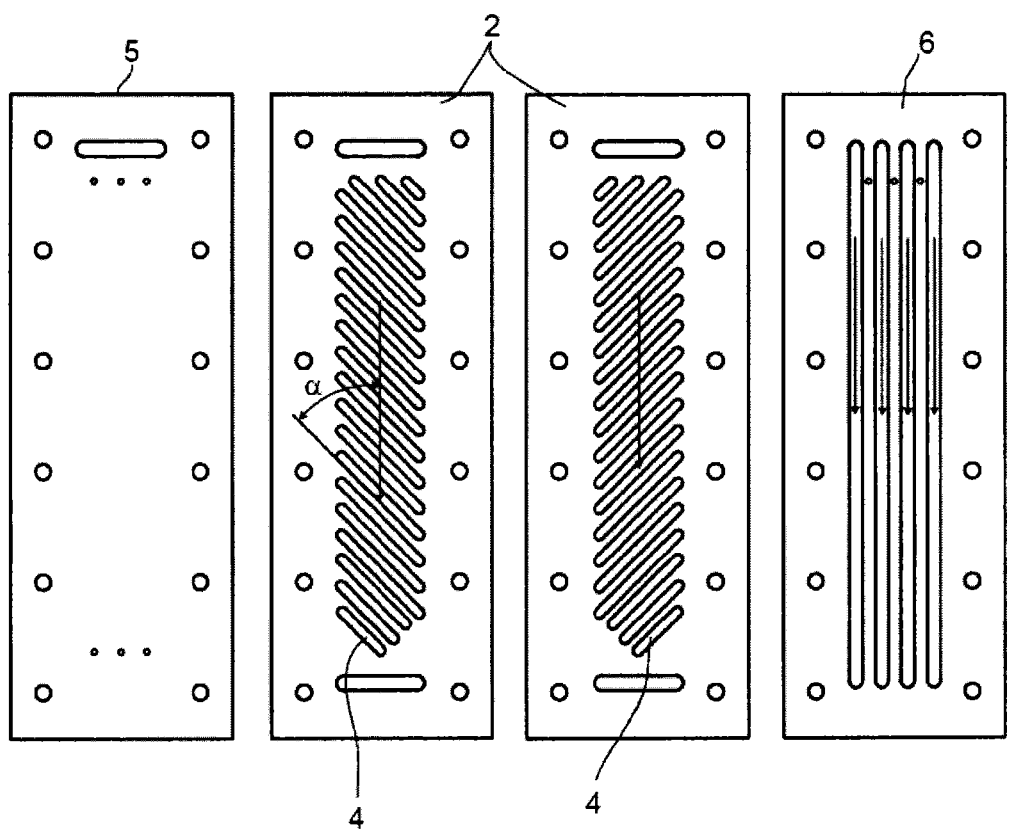

In the drawing, in detail:

FIG. 1 shows the schematic representation of one preferred embodiment of internals used in accordance with the invention, in a reaction unit, and FIG. 2 shows a schematic representation of individual plates of the internals depicted in FIG. 1.

The schematic representation in FIG. 1 shows a reaction unit 1 having internals 2 which are designed as two or more reaction plates 2 arranged in parallel above one another, in the principal direction of flow through the reaction unit 1, and which, together with separator sheets 5 arranged parallel thereto on both sides thereof, and with subsequent cooling or heating plates 6, form a reactor module 3. The starting materials are fed to the reaction plates 2, flow through them, and the product is taken off at the other end of the last reaction module. Cooling water, $H_2O$, flows through the cooling plates 6 in countercurrent to the reaction mixture.

The illustration in FIG. 2 shows the individual plates that form a reactor module 3, these being reaction plates 2 with slots 4, which are arranged at a nonzero angle α to the principal direction of flow, a separator sheet 5, and a cooling plate 6.

The examples of the invention were carried out in a Miprowa heat exchanger-reactor from BTS Ehrmann with internal dimensions of 1000*12*1.5 mm. As mixing elements, the reactor possessed three 0.5 mm comb layers having an internal surface area of 180 $cm^2$.

EXAMPLES

Example 1

Hydroxybutyl Vinyl Ether Ethoxylates

Under continuous flow, the sodium salt of a hydroxybutyl vinyl ether obtained from the reaction of vinyl ether with the corresponding amount of sodium methoxide in solution in methanol was introduced together with ethylene oxide directly into the microreactor described above.

The results of the experiment are apparent from Table 1 below:

TABLE 1

| | | | | | Product properties | | |
|---|---|---|---|---|---|---|---|
| Pressure [bar] | Temp. [° C.] | Residence time [min] | EO mol/ starter | Cat. conc. [%] | Viscosity 40° C. 0° C. [$mm^2$/s] | OH number [mg KOH/g] | Diol contents [%] |
| 40 | 150 | 23 | about 19 | 1.4 | 70 | — | — |

Example 2

Under continuous flow, a sodium methoxide solution which was converted to the alkoxide beforehand, in a deprotonation process, with a monofunctional starter, hydroxylbutyl vinyl ether, was introduced together with ethylene oxide directly into the microreactor described above.

The results of the experiment are apparent from Table 2 below:

TABLE 2

| | | | | | Product properties | | |
|---|---|---|---|---|---|---|---|
| Pressure [bar] | Temp. [° C.] | Residence time [min] | EO mol/ starter | Cat. conc. [%] | Viscosity 40° C. 0° C. [$mm^2$/s] | OH number [mg KOH/g] | Diol contents [%] |
| 40 | 150 | 23 | about 27 | 1.4 | 70 | 53 | — |

Example 3

Under continuous flow, a sodium methoxide solution which was converted to the alkoxide beforehand, in a deprotonation process, with a monofunctional starter, hydroxylbutyl vinyl ether, was introduced together with ethylene oxide directly into the microreactor described above.

The results of the experiment are apparent from Table 3 below:

TABLE 3

| | | | | | Product properties | | |
|---|---|---|---|---|---|---|---|
| Pressure [bar] | Temp. [° C.] | Residence time [min] | EO mol/ starter | Cat. conc. [%] | Viscosity 40° C. 0° C. [$mm^2$/s] | OH number [mg KOH/g] | Diol contents [%] |
| 40 | 180 | 13 | about 26 | 1.4 | 61 | 55 | 0.2 |

Example 4

Under continuous flow, a sodium methoxide solution which was converted to the alkoxide beforehand, in a deprotonation process, with a monofunctional starter, hydroxybutyl vinyl ether, was introduced together with ethylene oxide directly into the microreactor described above.

The results of the experiment are apparent from Table 4 below:

TABLE 4

| | | | | | Product properties | | |
|---|---|---|---|---|---|---|---|
| Pressure [bar] | Temp. [° C.] | Residence time [min] | EO mol/ starter | Cat. conc. [%] | Viscosity 40° C. 0° C. [mm$^2$/s] | OH number [mg KOH/g] | Diol contents [%] |
| 40 | 180 | 8 | about 25 | 1.4 | 66 | 56 | 0.1 |

Comparative Example 1

Polyether Polyols for Polyurethanes with KOH Catalysis

Under continuous flow, alkaline polyether (F=2.75, OH#=55.6, alkalinity 0.68%, catalyst KOH) and ethylene oxide were mixed in a static mixer (Ehrfeld) and then passed through a capillary without internals, having a volume of 6.1 ml (diameter: ¹⁄₁₆"). The reaction temperature was 170° C. and the conversion was complete. The residence time in the capillary was 1.8 minutes. A clear product was obtained.

TABLE 5

| Pressure [bar] | Temp. [° C.] | Residence time [min] | Mol EO/ mol starter | Cat. conc. [%] | Viscosity 50° C. [mPas] | OH number [mg KOH/g] |
|---|---|---|---|---|---|---|
| | 170 | 1.8 | about 20 | 0.68 | 588 | 42.3 |

Example 5

Polyether Polyols for Polyurethanes with KOH Catalysis

Under continuous flow, alkaline polyether (F=2.75, OH#=55.6, alkalinity 0.67%, catalyst KOH) and ethylene oxide were mixed in a static mixer (Ehrfeld) and then fed into a Miprowa reactor from BTS Ehrmann with inventive internals. The reaction temperature was 170° C. and the conversion was complete. The residence time in the capillary was 1.8 minutes. A clear product was obtained.

TABLE 6

| Pressure [bar] | Temp. [° C.] | Residence time [min] | Mol EO/ mol starter | Cat. conc. [%] | Viscosity 50° C. [mPas] | OH number [mg KOH/g] |
|---|---|---|---|---|---|---|
| | 170 | 1.8 | about 20 | 0.67 | 432 | 42.0 |

Example 6

Polyether Polyols for Polyurethanes with KOH Catalysis

Under continuous flow, alkaline polyether (F=2.75, OH#=55.6, alkalinity 0.68%, catalyst KOH) and ethylene oxide were mixed in a static mixer (Ehrfeld) and then fed into a Miprowa reactor from BTS Ehrmann with inventive internals. The reaction temperature was 170° C. and the conversion was complete. The residence time in the capillary was 1.8 minutes. A clear product was obtained.

TABLE 7

| Pressure [bar] | Temp. [° C.] | Residence time [min] | Mol EO/ mol starter | Cat. conc. [%] | Viscosity 25° C. [mPas] | OH number [mg KOH/g] |
|---|---|---|---|---|---|---|
| | 170 | 1.8 | about 10 | 0.68 | 1441 | 47.9 |

Example 7

Polyether Polyols for Polyurethanes with KOH Catalysis

Under continuous flow, alkaline polyether (F=2.75, OH#=55.6, alkalinity 0.68%) and propylene oxide were mixed in a static mixer (Ehrfeld) and then fed into a Miprowa reactor from BTS Ehrmann with inventive internals. The reaction temperature was 170° C. and the conversion was complete. The residence time in the capillary was 1.8 minutes. A clear product was obtained.

TABLE 8

| Pressure [bar] | Temp. [° C.] | Residence time [min] | Mol PO/ mol starter | Cat. conc. [%] | Viscosity 25° C. [mPas] | OH number [mg KOH/g] |
|---|---|---|---|---|---|---|
| | 150 | 1.8 | about 8.7 | 0.68 | 1007 | 46.5 |

Comparative Example 2

Polyether Polyols for Polyurethanes with DMC Catalysis

Under continuous flow, a DMC suspension in a trifunctional polypropylene oxide, Mw 3000, was premixed in an upstream stirring vessel having a volume corresponding to 6 times the volume of the microreactor, and then was introduced into a microreactor (crossflow reactor module having an integrated cyclone mixer, Forschungszentrum Karlsruhe (FZK), No. 1250-X-0.0). The reaction stopped repeatedly and resulted in only a low conversion.

Results of the experiment are set out in Table 9 below:

TABLE 9

| | | | | Product properties | | |
|---|---|---|---|---|---|---|
| Pressure [bar] | Temperature [° C.] | Residence time [min] | Cat. concentration [ppm] | Viscosity [25° C., mPas] | OH number | PO conc. [%] |
| 25 | 158 | 7 | 1080 | — | — | 85 |

Comparative Example 3

The experiment described under comparative example 2 was repeated, but the starting materials were premixed continuously in microstructured mixers, and specifically, first of all, propylene oxide and glycerol were introduced in a first micromixer (multilamination mixer, LH 25, Ehrfeld) and then in a second, identical micromixer the catalyst was introduced, and subsequently the reaction mixture was fed via a distributor chamber to the channels of a microreactor (cross-flow reactor module with integrated cyclone mixer, Forschungszentrum Karlsruhe (FZK), No. 1250-X-0.0.

The results of the experiment are set out in Table 10 below:

TABLE 10

| Pressure [bar] | Temperature [° C.] | Residence time [min] | Cat. concentration [ppm] | Product properties | | |
|---|---|---|---|---|---|---|
| | | | | Viscosity [25° C., mPas] | OH number | PO conc. [ppm] |
| 20 | 158 | 3 | 1050 | 2035 | 56.2 | 410 |

Example 8

The experiment described under comparative example 3 was repeated, but the starting materials were premixed continuously in microstructured mixers, and specifically, first of all, propylene oxide and glycerol were introduced in a first micromixer (multilamination mixer, LH 25, Ehrfeld) and then in a second, identical micromixer the catalyst was introduced, and subsequently the reaction mixture was fed to a microreactor (Miprowa reactor with inventive internals, BTS Ehrfeld). The results of the experiment are set out in Table 11 below:

TABLE 11

| Mixer type | Pressure [bar] | Temperature [min] | Residence time [min] | Cat. concentration [ppm] | Product properties | | |
|---|---|---|---|---|---|---|---|
| | | | | | Viscosity at 25° C. | OH number | PO conc. [ppm] |
| dyn. mixer (stirred autoclave) | 20 | 216 | 3 | 990 | 653 | 57.42 | 25 |
| dyn. mixer (stirred autoclave | 20 | 170 | 3 | 420 | 1085 | 53.2 | 60 |

Example 9

With Recirculation of Product

The experiments described under example 2 were repeated, but the DMC catalyst and recycled product from the microreactor were firstly premixed in a multilamination mixer (Ehrfeld, LH 25) and this product stream was subsequently mixed with propylene oxide and glycerol in a second mixer (Ehrfeld, LH 25). The reaction mixture was subsequently fed, as described in example 8, to a microreactor (Miprowa reactor with inventive internals, BTS-Ehrfeld).

The results are set out in Table 12 below:

TABLE 12

| Mixer type | Pressure [bar] | Temperature [min] | Residence time [min] | Cat. concentration [ppm] | Product properties | | |
|---|---|---|---|---|---|---|---|
| | | | | | Viscosity at 25° C. | OH number | PO conc. [ppm] |
| Multilamination mixer | 20 | 150 | 2.7 | 2200 | 617 | 56.2 | >1000 |

The invention claimed is:

1. A process for preparing polyether alcohols, the process comprising:
   reacting
   a) one or more alkylene oxides and optionally carbon dioxide, and
   b) one or more H-functional starter substances,
   in the presence of a catalyst, to form a liquid reaction mixture in a reaction unit,
   wherein:
   the reaction unit has internals which form a multiplicity of microstructured flow channels, which effect multiple splitting of the liquid reaction mixture into component flow pathways and renewed recombining thereof in altered arrangement,
   the multiple splitting and renewed recombining are repeated 10 to 10,000 times, and
   the microstructured flow channels having a characteristic dimension, defined as the greatest possible distance of any particle in the liquid reaction mixture to the flow channel wall closest to the particle, in a range of from 20 to 10,000 μm, so that a flow profile of the liquid reaction mixture through the microstructured flow channels is approximate to an ideal plug flow and away from a parabolic flow profile.

2. The process according to claim 1, wherein some or all of a) and b) and optionally the catalyst are premixed in a mixer outside the reaction unit at a temperature lower than a temperature of reacting.

3. The process according to claim 1, wherein the characteristic dimension of the microstructured flow channels is in a range of from 40 to 6000 μm.

4. The process according to claim 1, wherein:
the internals are reaction plates, with two or more of the reaction plates arranged in parallel above one another and in a principal direction of flow through the reactor unit to form a reactor module,
the reaction unit comprises one or more reactor modules,
each reaction plate comprises a multiplicity of slots of constant or variable width arranged parallel to one another and at a nonzero angle a to the principal direction of flow,
an immediately adjacent reaction plate comprises a multiplicity of geometrically identical slots arranged at an angle of −α,
the slots of all reaction plates are arranged one above another forming a flow channel,
a) and b) are fed into the flow channel and a product mixture is removed from the flow channel,
a separator sheet arranged parallel to each reaction plate and on both sides of the reactor module completely closes off the slots, and
a heat transfer medium circulates through one or more cooling or heating plates adjacent to each separator sheet on a side of the separator sheet opposite to the reactor module.

5. The process according to claim 4, wherein the angle α is 45°.

6. The process according to claim 4, wherein:
two or more cooling or heating plates are provided, with each cooling or heating plate comprising a multiplicity of slots of constant or variable width that are arranged parallel to one another and at the angle a to the principal direction of flow of the heat transfer medium,
an immediately adjacent cooling or heating plate comprises a multiplicity of geometrically identical slots arranged at the angle of −α, and
the slots of all the cooling or heating plates arranged one above another form a flow channel, with the heat transfer medium being fed into one end of the flow channel and removed at the other end of the flow channel.

7. The process according to claim 1, wherein the reaction of the one or more alkylene oxides takes place with addition of a comonomer or carbon dioxide, wherein the comonomer is a cyclic anhydride, a lactone, or any mixture thereof.

8. The process of claim 1,
wherein:
i) the reaction occurs in block operation with two or more reaction units,
ii) a) and b) are mixed in a ratio and fed to a first reaction unit to give a first reaction mixture,
iii) the first reaction mixture is optionally cooled or heated after leaving the first reaction unit,
iv) one or more additional materials either the same as or different from a) and b) are mixed in a mixing ratio different from the ratio in ii) to give a second reaction mixture, which is fed to a second reaction unit, and
v) the first and second reaction mixtures are fed to a third reaction unit, with iii) and iv) being repeated accordingly.

9. The process according to claim 2, wherein:
the one or more alkylene oxides, and optionally the carbon dioxide, are firstly premixed with the catalyst in a first mixing step in the mixer, and
the one or more H functional starter substances are mixed in a second mixing step.

10. The process according to claim 1, wherein a) are ethylene oxide, propylene oxide, butylene oxide, pentene oxide, glycidyl ether, hexene oxide, styrene oxide, carbon dioxide, or any mixtures thereof.

11. The process according to claim 1, wherein the H functional starter substances are one or more alcohols having a functionality of from 1 to 8.

12. The process according to claim 11, wherein
the alcohol having a functionality of 1 has the general formula R-OH, wherein R is a saturated or unsaturated alkyl, aryl, aralkyl or alkylaryl radical comprising 1 to 60.

13. The process according to claim 11, wherein the alcohols having a functionality of from 2 to 8 are ethylene glycol, propylene glycol, glycerol, trimethylolpropane, pentaerythritol, or any mixture thereof.

14. The process according to claim 1, wherein the catalyst is a multimetal cyanide complex catalyst.

15. The process according to claim 1, wherein the catalyst is potassium hydroxide, alkali metal alkoxide, or amine.

16. The process according to claim 14, wherein the multimetal cyanide complex catalyst is recovered by membrane crossflow filtration of a reaction discharge from the reaction unit and is recycled to the process.

17. The process according to claim 1, wherein the characteristic dimension of the microstructured flow channels is in a range of from 50 to 4000 μm.

18. The process according to claim 11, wherein the alcohol having a functionality of 1 is methanol, butanol, hexanol, heptanol, octanol, decanol, undecanol, dodecanol, tridecanol, tetradecanol, pentadecanol, hexadecanol, heptadecanol, octadecanol, butenol, hexenol, heptenol, octenol, nonenol, decenol, undecenol, vinyl alcohol, allyl alcohol, geraniol, linalool, citronellol, phenol, nonylphenol, or any mixture thereof.

* * * * *